United States Patent [19]

Magasi

[11] Patent Number: 4,810,376
[45] Date of Patent: Mar. 7, 1989

[54] MEDICAL BAG ARRANGEMENT

[76] Inventor: Josef Magasi, Wendelinusstrasse 8, D-6902 Sandhausen, Fed. Rep. of Germany

[21] Appl. No.: 866,164

[22] Filed: May 22, 1986

[30] Foreign Application Priority Data

May 23, 1985 [DE] Fed. Rep. of Germany ... 8515209[U]

[51] Int. Cl.⁴ .............................................. B01D 13/00
[52] U.S. Cl. ................................. 210/136; 210/321.69
[58] Field of Search ....................... 206/438; 604/410; 222/94; 220/20.5; 210/321.3, 321.2, 321.1, 136, 321.69

[56] References Cited

U.S. PATENT DOCUMENTS

| 4,014,461 | 3/1977 | Harvill .................................. 222/94 |
| 4,403,992 | 9/1983 | Bertellini ............................. 604/410 |

FOREIGN PATENT DOCUMENTS

| 0090093 | 10/1983 | European Pat. Off. . |
| 8106491 | 10/1981 | Fed. Rep. of Germany . |
| 8515209 | 9/1985 | Fed. Rep. of Germany . |
| 2566273 | 12/1985 | France . |

Primary Examiner—Frank Spear
Attorney, Agent, or Firm—Andrus, Sceales, Starke & Sawall

[57] ABSTRACT

Medical bag arrangement (10, 70) comprising a first bag chamber (12, 72) and a second bag chamber (14, 74), the first bag chamber (12, 72) being filled with a flushing liquid. From the first bag chamber (12, 72) an outlet line (80) branches and an inlet line (86) opens into the second bag chamber (74). Furthermore, from the inlet line (86) to the first bag chamber (72) an overflow line (92) leads into which a pressure control valve (94) is connected.

8 Claims, 2 Drawing Sheets

MEDICAL BAG ARRANGEMENT

The invention relates to a medical bag arrangement formed of an organic polymer for use in flushing out an apparatus for treating the human body comprising a first bag chamber and a second bag chamber, the first bag chamber being filled with a flushing liquid and having an outlet line and the second bag chamber having an inlet line.

Numerous acute and chronic diseases exist which require treatment of body fluids outside the body in extracorporeal cycle. Such treatments are carried out in hemodialysis or hemofiltration, the blood being subjected to the dialysis treatment in a dialyzer.

Such dialyzers generally comprise a great number of membranes which divide the dialyzer into a chamber traversed by blood and a chamber traversed by dialysis solution.

Such capillary or plate dialyzers are sterilized by the manufacturers themselves, for example by treating with ethylene oxide or by irradiation with sterilizing radiation, and conserved with the aid of a conserving agent, for example glycerol. They are then used at the bedside when required, it being necessary to flush such blood treatment apparatuses before use to remove the adhering chemicals, in particular the conservation or preservation agents.

For this purpose the blood side of the dialyzer is connected to a blood tubing system having an arterial and a venous side, the ends thereof each comprising a connector piece for receiving the needles. One side of the blood tubing system is inserted into a peristaltic pump and the two ends of the blood tubing system are connected to a bag containing for example a flushing liquid, for example a saline solution. Thereafter the saline solution is pumped through the dialyzer, the dialyzer simultaneously being filled with the physiological saline solution and rinsed free of the adhering chemicals.

A disadvantage in this arrangement is however that the flushing liquid mixed with the chemicals on return to the bag becomes mixed with fresh flushing liquid so that the substances to be removed from the dialyzer can again enter the flushing circulation.

For this reason a bag arrangement has been proposed in which the bag containing the flushing liquid is kept separate from the bag containing the used flushing liquid. This has the advantage that the fresh flushing liquid no longer comes into contact with the used flushing liquid but the disadvantage that the flushing operation itself must be monitored by the operator because otherwise there is a danger of the bag with the used flushing liquid bursting and the entire arrangement running empty, which apart from the undesired filling of the dialyzer with air also involves sterility problems.

The invention is therefore based on the need of further developing the bag arrangement of the type mentioned at the beginning so that a dialyzer connected thereto can be flushed and filled without monitoring measures.

This problem is solved according to a first independent embodiment in that the first bag chamber comprises an overflow line which is connected to the inlet line and that in the overflow line a valve opening at a predetermined excess pressure is provided, and according to a second independent embodiment in that the inlet line extends through the first bag chamber and that the inlet line in the region of the first bag chamber comprises a valve opening at a predermined excess pressure.

The bag arrangement according to the invention has the advantage that after connecting to the dialyzer and starting operation of the peristaltic pump it need no longer be supervised by the operator. The pump takes from the first bag chamber fresh flushing liquid and leads it on the blood side of the dialyzer along the membrane wall, thereby leaching out of the membrane at the start of the flushing treatment substances disposed in the membrane, for example glycerol or sodium acetate. The flushing liquid charged with these substances leaves the dialyzer and returns to the bag arrangement into the second bag chamber, the latter being filled with used flushing liquid. The filling of the second bag chamber can take place only until the entire internal volume available is occupied. After that the internal pressure in the bag increases abruptly which would normally lead to bursting of the bag and stopping of the flushing step. Since however according to the invention in the region of the inlet line to the second bag chamber a pressure control valve is provided, the flushing fluid can escape through said pressure control valve.

According to a particularly advantageous embodiment of the invention the inlet line is connected to an overflow line which opens into the first bag chamber. The pressure control valve is provided in the overflow line so that after complete filling of the second bag chamber with used flushing liquid, substantially uncontaminated flushing liquid can flow through the inlet line and the overflow line into the first bag chamber, the flow cycle being closed because at the same time practically all unused flushing liquid is withdrawn from the first chamber.

It has been found that the flushing liquid amount to be pumped into the second bag chamber suffices to free the dialyzer effectively from the conservation substances. Accordingly, after the filling of the second bag chamber practically pure flushing liquid is withdrawn via the overflow line. It should be noted that the entire system is closed with respect to the surroundings, i.e. the sterile state is maintained during flushing.

As flushing liquid normally physiological saline solution, 0.9% NaCl solution or 5% Levulose solution is used which is also employed to fill the blood tubing system and the blood-side chamber of the dialyzer.

Dialysis filters are sterilized dry by the manufacturers either with ethylene oxide or gamma rays or are filled and autoclaved with distilled water. The manufacturer suggests that the first 300–500 ml flushing liquid in the flushing treatment of these filters be discarded because this guarantees that the glycerol contained in the membrane and serving to preserve said membrane and residual particles contained in the filter are flushed out of the system. Accordingly after removal of the 300–500 ml the venous part of the blood tubing system was coupled to the bag containing the flushing liquid and the aforementioned recirculation operation was thereby started. It would be superfluous to explain that this results in sterility problems.

With the bag arrangement according to the invention this expenditure of work and time is superfluous because the perfusion operation runs automatically so that the operator need only connect the two ends of the blood tubing system to the bag arrangement according to the invention. The rest of the flushing operating takes place automatically without supervision.

Advantageously, the ends of the inlet line and the outlet line are each provided with a connector which is complementary with the connectors provided at the ends of the blood tubing system. After the perfusion treatment the connections are detached again and the ends of the blood tubing lines are each provided with a needle.

Further advantages, details and features of the invention will be explained with the aid of the following description of two examples of embodiment with reference to the drawings, wherein:

FIG. 1 shows a bag arrangement (10) having a first bag chamber (12) and a second bag chamber (14). The two bag chambers (12) and (14) in the embodiment shown in FIG. 1 are separated by a common fusion or weld line (16) and consequently form a single bag unit which is surrounded by a common weld edge (18).

Figure 1:
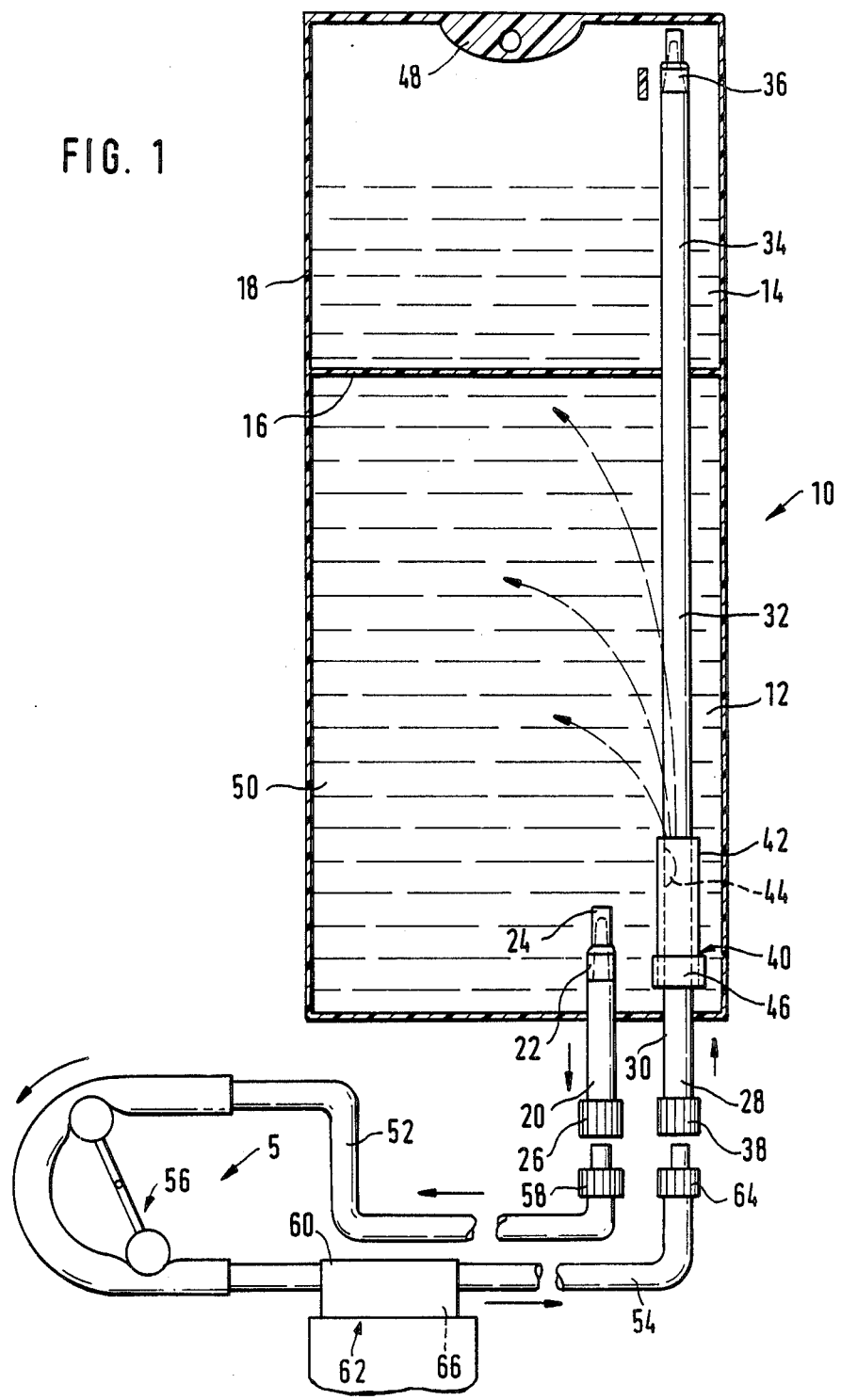
FIG. 1 shows schematically a first embodiment of the invention in cross-section and FIG. 2 shows a second embodiment of the bag arrangement according to the invention in cross-section.

The first bag chamber (12) comprises an outlet line (20) which in accordance with the embodiment shown in FIG. 1 is welded into the weld edge (18) and through said weld edge opens into the first bag chamber (12), thus connecting the latter to the environment.

In the unused state the outlet line (20) comprises on the inner side of the first bag chamber (12) a break-off portion (22) whose end (24) can be broken off in a manner known per se so that thereby a flow connection is established between the first bag chamber (12) and the environment.

Furthermore, the end of the outlet line (20) disposed outside the first bag chamber (12) comprises a connector piece (26) which in the unused state is sealed in sterile manner with a cap.

The second bag chamber (14) comprises on the other hand an inlet line (28) which in accordance with the embodiment shown in FIG. 1 passes through the first bag chamber (12) into the second bag chamber (14) so that the inlet line consists of the following parts:

An inlet piece (30) dispose outside the bag arrangement (10), a passage piece (32) disposed in the first bag chamber (12) and an end piece (34) which leads into the second bag chamber (14) and the end of which is connected to a second break-off portion (36) which is handled like the break-off portion (22) described above.

The inlet line (28) is welded in each case with the encircling weld edge (18) and the separating weld line (16) so that between the two bag chambers (12) and (14) and towards the environment no liquid exchange is possible.

Finally, the end of the inlet piece (30) is connected to a second connector piece (38) which corresponds in its function to the connector piece (26).

According to the embodiment of the bag arrangement (10) shown in FIG. 1 the inlet line is provided in the region of the first bag chamber (12), i.e. the passage piece (32) with a valve (40) which responds to a predetermined excess pressure and which in accordance with the embodiment shown in FIG. 1 is constructed as resilient flexible tube section which bears resiliently sealingly on the passage piece (32) and covers an opening (44) disposed in the passage piece (32). Advantageously, the flexible tube section (42) is fixed with the aid of a fixing member (46) on the passage piece (32) and thus cannot axially shift.

The bag arrangement (10) may be made from plastic materials known per se, for example PVC, polyethylene, polypropylene and the like, these inner materials usually being laminated on the outside with a covering film of for example polyamide.

Furthermore, as shown in FIG. 1 the bag arrangement (10) may comprise on its upper side a suspension eye (48) with which the bag arrangement (10) can be suspended on a stand, not shown.

Finally, the first bag chamber (12) is filled with a flusing liquid (15), the capacity of the first chamber being about 1–1.5 l. The capacity of the second chamber (14) is however about 0.3–0.5 l.

The bag arrangement (10) can be connected to a perfusion means (5) which generally consists of a blood tubing system having an arterial branch (52) and a venous branch (54). Generally, a peristaltic pump (56) is connected into the arterial branch. The one end of the arterial branch comprises a connector piece (58) which is a complementary fit with the connector (26). On the other hand the other end of the arterial branch is connected to the chamber (60) of the dialyzer (62) adapted to receive blood. The outlet of the chamber (60) adapted to receive blood is connected to the one end of the venous branch (54) whose other end is connected to a further connector piece (64) which is complementary to the connector piece (38).

Finally, the chamber of the dialyzer (62) designated by (66) and traversed by dialysis solution is shown, the direction of flow of the dialysis solution being indicated by the direction of the arrow.

The arrangement shown in FIG. 1 is operated as follows:

Firstly, the blood tubing system consisting of the venous and arterial branches (52) and (54) are connected to the dialyzer and inserted into the pump (56). Then, the corresponding connector pieces (26) and (58) and (38) and (64) respectively, are connected together to give a closed system. Finally, the break-off portions (22) and (36) are broken off so that the first bag chamber is brought into flow connection through the blood tubing system and the dialyzer with the second bag chamber (14). Thereafter, the pump (56) is set in operation, firstly the entire air being expelled from the blood tubing system and the dialyzer and collecting in the second bag chamber (14). Thereafter, the arterial branch (52), the blood chamber (60) of the dialyzer (62) and the venous branch become filled with flushing liquid which finally rises in the inlet line (28) and thereafter collects in the second bag chamber (14). This filling step lasts until the entire internal volume available of the second bag chamber (14) is almost full with the flushing liquid, the air collected in the second bag chamber (14) being compressed by the flushing liquid. As a result, the internal pressure slowly increases up to the value corresponding to the opening value of the valve (40). This is usually at an excess pressure of 0.1–0.3 bar. As soon as this excess pressure is reached, the valve (40) opens and the flushing liquid recycles back into the first bag chamber (12) whilst the used flushing liquid charged with the conservation agent remains in the second chamber (14) and because of the pressure relationships does not flow back to the valve (40). Accordingly, after the opening of the valve (40) substantially only fresh flushing liquid is withdrawn at the bottom of the first chamber (12) and conducted continuously through the dialyzer (62).

After a certain perfusion duration the pump (56) is stopped and the connector parts (26, 58) and (38, 64) are separated from each other, the connector pieces (58) and (64) thereafter being provided with needles which are then injected into the patient in a manner known per se.

Figure 2:
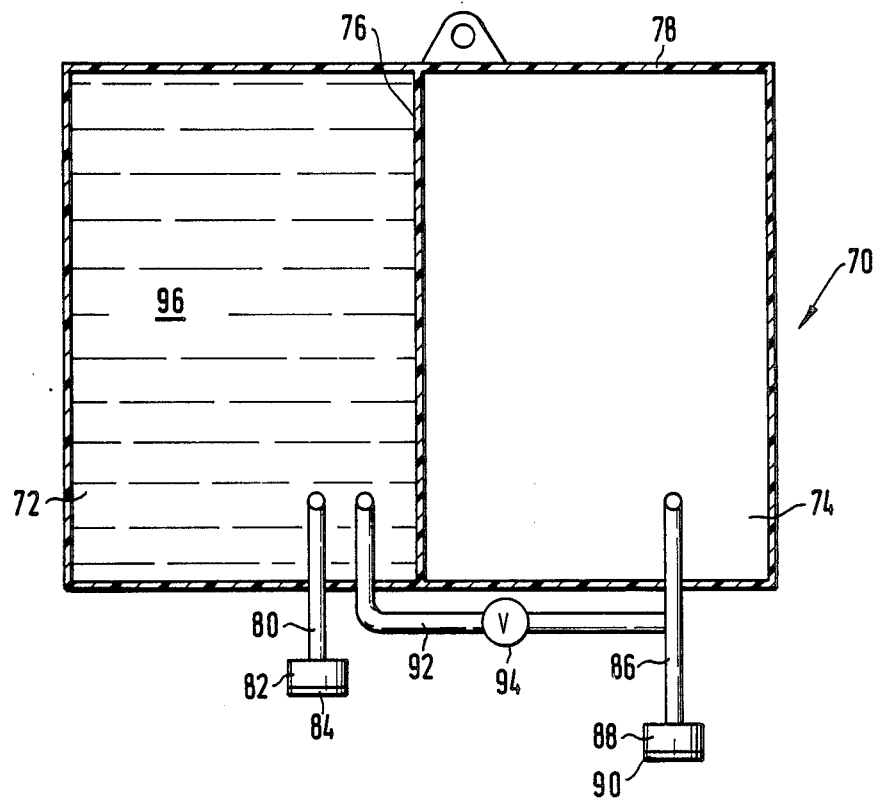

FIG. 2 shows a second embodiment of a bag arrangement (70). This bag arrangement (70) comprises a first bag chamber (72) and a second bag chamber (74) which also have a joint weld line (76). However, according to a further embodiment the two bag chambers (72) and (74) may also be in the form of a single bag, i.e. the common weld line (76) is no longer provided in this embodiment. Furthermore, the bag arrangement (70) is provided with an encircling weld edge (78).

An outlet line (80) opens into the first bag chamber (72) and comprises at its end lying outside the bag chamber a connector piece (82) which is provided with a pierceable membrane (84).

The second bag chamber (74) comprises an inlet line (86) which is welded like the outlet line (80) into the bag edge (78) and traverses the latter and opens into the second bag chamber (74). This inlet line (86) also comprises at its end lying outside the second bag chamber (74) a connector piece (88) which likewise comprises a pierceable membrane (90) at its end.

Branching from the inlet line (86) outside the second bag chamber (18) is an overflow line (92) whose end opens into the first bag chamber (72), the end of the overflow line (92) being welded into the weld edge (78) and led through the latter. Furthermore, a valve (94) opening at a predetermined pressure is connected into the overflow line (92), the function of said valve corresponding to that of the valve (40) which has been described above. The valve can advantageously be constructed as a conventional check valve sealed in sterile manner from the outside and opening under spring action at a predetermined excess pressure, for example at the excess pressure outlined above.

Furthermore, in the first bag chamber a flushing solution (96) is provided which corresponds to the flushing solution (50) described above.

The two connector pieces (82) and (88) can be connected to the connector pieces (58) and (64) of the arterial and venous blood line (52) and (54) providing these connector pieces are connected to the needle fittings to enable the pierceable membranes (84) and (90) to be pierced. On the other hand, these pierceable membranes need not be provided so that the connector pieces (82) and (88) fit together similarly to the connector pieces (26) and (38) in complementary manner in accordance with the first embodiment illustrated in FIG. 1. In this respect the break-off portions (22) and (36) may also be provided in the outlet and inlet lines (80) and (86).

Essential in this second embodiment is the separate arrangement of the two lines (80) and (86), an overflow line (92) leading from the inlet line (86) to the first bag chamber (72) and being brought into operation at a predetermined excess pressure by the pressure control valve (94) included therein. The mode of operation of the embodiment shown in FIG. 2 corresponds to the mode of operation of the embodiment shown in FIG. 1 so that reference may be made to the description thereof. Thus, the outlet line (80) is connected to the arterial flexible tube section (52) whilst the inlet line (86) is connected to the venous flexible tube section (54). By the action of the pump (56) the first bag chamber (72) is evacuated, at the same time the second bag chamber (74) being filled until its filling capacity is used up. Thereafter the pressure control valve (94) preferably constructed as check valve opens, the circulated flushing liquid being pumped via the inlet line (86) and the overflow (92) into the first bag chamber (72) and from there again in a recirculation through the out line (80) to the dialyzer (62). After completion of the perfusion the connectors are detached, the further procedure being as usual.

I claim:

1. A medical bag formed of an organic polymer and usable to flush apparatus (62) for treating the human body, said bag comprising:
    a first bag chamber (12; 72) filled with a flushing liquid (50; 96), said first bag chamber having an outlet line (20; 80) for supplying liquid to the apparatus;
    a second bag chamber (14; 74) having an inlet line (28; 86) communicating therewith for receiving liquid from the apparatus;
    a connecting means (44; 92) forming a fluid communication between said inlet line (28; 86) and said first bag chamber (12; 72); and
    a closure member (40; 94) disposed in said connecting means (44; 92), said closure member comprising positive pressure responsive value means (40; 94) automatically openable after a predetermined positive pressure has been reached within said second bag chamber (14; 74) to provide liquid in said inlet line through said connecting means to said first bag chamber, said positive pressure being created by the compression of air within said second bag chamber (14; 74) by the liquid received in said second bag chamber from the apparatus.

2. A medical bag according to claim 1 wherein said connecting means comprises an opening (44) disposed in said inlet line (28) and communicating with said first bag chamber (12).

3. A medical bag according to claim 2 wherein said valve means (40) comprises a flexible tube section (42), resiliently engaged around the inlet line (28) and covering said opening (44).

4. A medical bag according to claim 1, wherein said valve means (40; 94) comprises a check valve operable by positive pressure.

5. A medical bag according to claim 1 wherein said outlet line (20; 80) and said inlet line (28; 86) have ends lying in the respective bag chambers (12, 14, 72, 74), said ends having break-off portions (22, 36) permitting said lines to communicate with the chambers.

6. A medical bag according to claim 1 wherein said outlet line (20; 80) and said inlet line (28; 86) have ends disposed outside the bag chambers (12, 72, 14, 74), said ends having connector elements (26, 38, 88) connectable in complementary manner to connector pieces (58, 64) disposed on the apparatus.

7. A medical bag according to claim 1 wherein said first bag chamber (12; 72) has a capacity of about 1–1.5 liters and said second bag chamber (14; 74) has a capacity of about 0.3–0.5 liters.

8. A medical bag according to claim 1 wherein said valve means (40; 94) opens at a positive pressure increase of 0.1–0.3 bar.

* * * * *